(12) United States Patent
Mauro

(10) Patent No.: US 6,792,952 B2
(45) Date of Patent: Sep. 21, 2004

(54) METHOD AND DEVICE FOR TREATMENT OF TEMPOROMANDIBULAR DYSFUNCTION SYNDROME AND FACIAL/DENTAL DEFORMITIES

(76) Inventor: Joseph V. Mauro, 631 Applegate La., East Lansing, MI (US) 48823

( * ) Notice: Subject to any disclaimer, the term of this patent is extended or adjusted under 35 U.S.C. 154(b) by 246 days.

(21) Appl. No.: 10/140,093

(22) Filed: May 7, 2002

(65) Prior Publication Data

US 2003/0211441 A1 Nov. 13, 2003

(51) Int. Cl.[7] ............................................. A61C 5/14
(52) U.S. Cl. ..................................... 128/859; 128/861
(58) Field of Search ............................... 128/846, 848, 128/859–862; 433/6; 602/902

(56) References Cited

U.S. PATENT DOCUMENTS

| | | | |
|---|---|---|---|
| 4,034,475 A | | 7/1977 | Lee |
| RE31,615 E | | 6/1984 | Lee |
| 4,909,737 A | | 3/1990 | Lee |
| 5,092,346 A | * | 3/1992 | Hays et al. .................. 128/848 |
| 5,566,683 A | * | 10/1996 | Thornton ..................... 128/848 |
| 6,055,986 A | * | 5/2000 | Meade ......................... 128/848 |
| 6,109,917 A | | 8/2000 | Lee et al. |
| 6,729,335 B1 | * | 5/2004 | Halstrom ..................... 128/848 |

OTHER PUBLICATIONS

Kelly in Atlas of Oral and Maxillofacial Surgery (Keith ed., W.B. Saunders Company, Philadelphia, (1992) pp. 73086.

* cited by examiner

Primary Examiner—Michael A. Brown
(74) Attorney, Agent, or Firm—Ian C. McLeod

(57) ABSTRACT

A method for treating maxilla/cranial base to mandibular axis discrepancies in the temporomandibular joints (TMJs) of a patient such as caused by mandibular, temporomandibular dysfunction syndrome (MTDS) or developmental facial/dental deformities without performing open jaw joint surgery. The method includes (1) repositioning the patient's mandible into a stable relationship with the cranial base using a craniomandibular orthopedic repositioning orthotic which over time deprograms the patient's jaw into the stable mandible to cranial base relationship; (2) constructing a model of the patient's mouth on a jaw joint simulator which replicates the patient's jaw joint true hinge axis of rotation in the repositioned and stabilized mandible to cranial base relationship; (3) planning on the model a surgical procedure comprising total maxillary osteotomy which substantially treats the MTDS or developmental facial/dental deformities; and (4) performing the surgical procedure to treat the discrepancies.

7 Claims, 9 Drawing Sheets

METHOD AND DEVICE FOR TREATMENT OF TEMPOROMANDIBULAR DYSFUNCTION SYNDROME AND FACIAL/DENTAL DEFORMITIES

CROSS-REFERENCE TO RELATED APPLICATION

Not applicable.

STATEMENT REGARDING FEDERALLY SPONSORED RESEARCH OR DEVELOPMENT

Not applicable.
Reference to a "Computer Listing Appendix Submitted on a Compact Disc"
Not applicable.

BACKGROUND OF THE INVENTION (1) Field of the Invention

The present invention relates to a method for treating maxilla/cranial base to mandibular axis discrepancies in the temporomandibular joints (TMJs) of a patient such as is caused by mandibular, temporomandibular dysfunction syndrome (MTDS) or developmental facial/dental deformities without performing open jaw joint surgery. The method includes (1) repositioning the patient's mandible into a stable relationship with the cranial base using a craniomandibular orthopedic repositioning orthotic which over time deprograms the patient's jaw into the stable mandible to cranial base relationship; (2) constructing a model of the patient's mouth on an artificial jaw simulator which replicates the patient's jaw joint true hinge axis of rotation in the repositioned and stabilized mandible to cranial base relationship; (3) planning a surgical procedure comprising total maxillary osteotomy on the model which substantially treats the MTDS or developmental facial/dental deformities; and (4) performing the surgical procedure on the patient based on the surgical procedure planned on the model to treat the discrepancies.

(2) Description of Related Art

The surgical treatment of mandibular, temporomandibular dysfunction syndrome (MTDS) or developmental facial/dental deformities traditionally has centered on surgical manipulation of the jaw joint structural components: disc, ligaments, and tendons using open arthrotomy, arthroscopy, or partial or total jaw joint replacement. The fundamentals of oral and maxillofacial surgical procedures are standard and have been described in many texts on surgical techniques. For example, see *Atlas of Oral and Maxillofacial Surgery* (Keith ed., W. B. Saunders Company, Philadelphia, (1992) pp. 201–216). In general, these surgical procedures are performed with the jaw joints in an acquired bite or position of maximum intercuspation of the teeth without reference to the relationship of each mandibular condyle to its socket of the glenoid fossa and without any attempt to place each mandibular condyle in any stable, verifiable, and reproducible position in its socket of the glenoid fossa. Furthermore, the surgical procedures for treating MTDS or developmental facial/dental deformities are not generally planned on a model of the patient's jaw joint in which the model has replicated the patient's true hinge axis of rotation in the stable condylar position. Because the mandible condyles are not stably positioned within their sockets, the mandible to cranial base relationship remains unstable. Therefore, following a standard surgery for treating MTDS or developmental facial/dental deformities, the unstable relationship between the mandible and cranial base over time tends to develop into MTDS. As long as the relationship between the mandible and cranial base remains unaddressed in the standard surgical treatments for MTDS or developmental facial/dental deformities, the unstable relationship will remain and most likely render the surgical treatment merely temporary in effect.

Therefore, there is a need for a surgical method for treating MTDS or developmental facial/dental deformities in a patient wherein the method restores a functional bite to the patient while maintaining the patient's jaw joint in its stable condylar position. In particular, there is a need for a method wherein the surgery to treat the MTDS or the developmental facial/dental deformities is planned on a model which replicate's the patient's true hinge axis of rotation in which the mandibular condyles are in a stable condylar position.

SUMMARY OF THE INVENTION

The present invention provides a method for treating maxilla/cranial base to mandibular axis discrepancies in the temporomandibular joints (TMJs) of a patient such as is caused by mandibular, temporomandibular dysfunction syndrome (MTDS) or developmental facial/dental deformities without performing open jaw joint surgery. The method includes (1) repositioning the patient's mandible into a stable relationship with the cranial base using a craniomandibular orthopedic repositioning orthotic which over time deprograms the patient's jaw into the stable mandible to cranial base relationship; (2) constructing a model of the patient's mouth on an artificial jaw simulator which replicates the patient's jaw joint true hinge axis of rotation in the repositioned and stabilized mandible to cranial base relationship; (3) planning a surgical procedure comprising total maxillary osteotomy on the model which substantially treats the MTDS or developmental facial/dental deformities; and (4) performing the surgical procedure on the patient based on the surgical procedure planned on the model to treat the discrepancies.

Therefore, the present invention provides a method for treating maxilla/cranial base to mandibular axis discrepancies in the temporomandibular joints of a patient comprising (a) fitting an orthotic to the maxillary teeth of the patient so as to allow full coverage of all the maxillary teeth, wherein the orthotic has an anterior ramp to provide anterior guidance of the patient's mandible in excursive movements by contact of the superior surface of the anterior mandibular teeth of the patient with a posterior surface of the anterior ramp of the orthotic so as to allow for complete disclusion of the posterior mandibular teeth of the patient from the orthotic during eccentric jaw movements which over time deprograms the temporomandibular joints of the patient into a stable condylar position by stabilizing the condyles in their corresponding glenoid fossa sockets in the maxilla/cranial base;

(b) determining alignment of the mandible to the maxilla/cranial base in the temporomandibular joints of the patient after each condyle has been stabilized in its corresponding glenoid fossa socket by the orthotic;

(c) constructing a model of an upper dental arch of the patient with a base, which is parallel on all sides to the upper dental arch model and is delineated with horizontal and vertical reference lines, and a model of a lower dental arch of the patient with a base, which is parallel on all sides to the lower dental arch model and is delineated with horizontal and vertical reference lines;

(d) mounting the base of the upper dental arch to an upper plate with mounting stone of an artificial jaw simulator and mounting the base of the lower dental arch to a lower plate with mounting stone of the artificial jaw simulator such that the true axis of rotation of the temporomandibular joints of the patient with the temporomandibular joints in the stable condylar position has been maintained and wherein the sides of each base are parallel and confluent to the artificial jaw simulator mounting plates;

(e) determining on the artificial jaw simulator mounted with the upper and lower dental arch models an amount of maxillary bone to be removed from the patient's maxilla in a surgical procedure wherein the maxilla is cut along a transverse plane superior to the maxillary teeth to separate the maxilla into an upper and a lower part which is sufficient to allow a jaw position in the patient when the upper and lower parts are joined after the amount of maxillary bone has been removed wherein the maxillary and mandibular teeth of the patient are re-approximated into a position coincidental to the stabilized jaw joint position with a functional bite wherein the anterior maxillary teeth provide anterior guidance of the mandible in excursive movements by contact of the lingual surface of the anterior maxillary teeth with the superior surface of the mandibular anterior teeth while allowing complete disclusion of the posterior maxillary and mandibular teeth during eccentric jaw movements and which at the same time maintains the temporomandibular joints in the stable condylar position;

(f) constructing a surgical stint of the functional bite in which the temporomandibular joints are in the stable condylar position to act as a guide for relating the maxilla to the mandible during the surgical procedure for removing the amount of maxillary bone from the patient determined in step (e);

(g) fitting the surgical stint into the mouth of the patient and performing the surgical procedure for removing the amount of maxillary bone from the patient's maxilla determined in step (e); and (h) immobilizing the patient's jaw following the surgical procedure with the surgical stint fitted to the patient's teeth so as to maintain the functional bite wherein the temporomandibular joints are in the stable condylar position and fixating the patient's mouth shut for a time sufficient for the upper and lower parts of the maxilla to heal, which treats the cranial base to the mandibular axis discrepancies in the temporomandibular joints.

In a further embodiment of the method, the surgical procedure further includes an interim surgical procedure selected from the group consisting of widening the patient's mandible, widening the patient's maxilla, retruding the patient's mandible, advancing the patient's mandible, retruding the patient's maxilla, advancing the patient's maxilla, and combinations thereof and an intermediate surgical stint is made to act as a guide for relating the maxilla to the mandible during the interim surgical procedure.

In a further embodiment of the above methods, the temporomandibular joints of the patient are stabilized by sequentially fitting orthotics to the patient's mouth wherein the anterior ramp of each orthotic in the sequence has been progressively elongated or wherein the orthotic is modified by elongating the anterior ramp or reducing the thickness of the orthotic covering the posterior maxillary teeth when needed to maintain complete disclusion of the posterior maxillary and mandibular teeth of the patient during eccentric jaw movements during the period of time for deprogramming the temporomandibular joints into the stable condylar position.

The present invention further provides a surgical method for treating the cranial base to mandibular axis discrepancies in a patient comprising:

(a) constructing a model of an upper dental arch of the patient with a base, which is parallel on all sides to the upper dental arch model and is delineated with horizontal and vertical reference lines, and a model of a lower dental arch of the patient with a base, which is parallel on all sides to the lower dental arch model and is delineated with horizontal and vertical reference lines;

(b) mounting the upper dental arch to an upper plate with mounting stone of an artificial jaw simulator and mounting the lower dental arch to a lower plate with mounting stone of the artificial jaw simulator such that the true axis of rotation of the temporomandibular joints of the patient with the temporomandibular joints in the stable condylar position has been maintained and wherein the sides of each base is parallel and confluent to the artificial jaw simulator mounting stones;

(c) determining on the artificial jaw simulator mounted with the upper and lower dental arch models an amount of maxillary bone to be removed from the patient's maxilla in a surgical procedure wherein the maxilla is cut along a transverse plane superior to the maxillary dentition to separate the maxilla into an upper and a lower part which is sufficient to allow a jaw position in the patient when the upper and lower parts are joined after the amount of maxillary bone has been removed wherein the dentition of the patient is re-approximated into a functional bite wherein the anterior maxillary teeth provide anterior guidance of the mandible in excursive movements by contact of the lingual surface of the anterior maxillary teeth with the superior surface of the central and lateral incisors while allowing complete disclusion of the posterior maxillary and mandibular teeth during eccentric jaw movements and which at the same time maintains the temporomandibular joints in the stable condylar position;

(d) constructing a surgical stint of the functional bite in which the temporomandibular joints are in the stable condylar position to act as a guide for relating the maxilla to the mandible during the surgical procedure for removing the amount of maxillary bone from the patient determined in step (c);

(e) fitting the surgical stint into the mouth of the patient and performing the surgical procedure for removing the amount of maxillary bone from the patient's maxilla determined in step (c); and (f) immobilizing the patient's jaw following the surgical procedure with the surgical stint fitted to the patient's teeth so as to maintain the functional bite wherein the temporomandibular joints are in the stable condylar position and fixating the patient's mouth shut for a time sufficient for the upper and lower parts of the maxilla to heal, which treats the cranial base to the mandibular axis discrepancies in the temporomandibular joints.

In a further embodiment of the method, the surgical procedure further includes an interim surgical procedure selected from the group consisting of widening the patient's mandible, widening the patient's maxilla, retruding the patient's mandible, advancing the patient's mandible, retruding the patient's maxilla, advancing the patient's maxilla, and combinations thereof and an intermediate surgical stint is made to act as a guide for relating the maxilla to the mandible during the interim surgical procedure.

The present invention further provides a method for stabilizing the condylar positions in the temporomandibular joints of a patient with temporomandibular dysfunction syndrome comprising:
(a) providing an orthotic to the maxillary teeth of the patient so as to allow full coverage of all the maxillary teeth, wherein the orthotic is designed with an anterior ramp to provide anterior guidance of the patient's mandible in excursive movements by contact of the superior surface of the mandibular anterior teeth of the patient with a posterior surface of the anterior ramp of the orthotic so as to allow for complete disclusion of the posterior mandibular teeth from the orthotic of the patient during eccentric jaw movements which enables deprogramming the temporomandibular joints into stable condylar position;
(b) fitting the orthotic into the patient's mouth for a period of time sufficient to deprogram the temporomandibular joints into the stable condylar position;
(c) modifying the orthotic when needed to maintain complete disclusion of the posterior maxillary and mandibular teeth of the patient during eccentric jaw movements during the period of time for deprogramming the temporomandibular joints into the stable condylar position; and
(d) measuring during the period of time for deprogramming the temporomandibular joints into the stable condylar position pain caused to the patient by the temporomandibular dysfunction, reproducibility of the patient's bite on the orthotic, neuromuscular tension of the patient's facial muscles, and the patient's condylar position indices, wherein the condylar positions in the temporomandibular joints of the patient are determined to be stabilized when the patient is free of the pain and has a reproducible bite on the orthotic, there is complete release of neuromuscular tension whereby the patient's facial muscles upon palpation show no signs of guarding, splinting, or tension, and the patient's condylar position indices are less than about 1 mm.

The present invention further provides an apparatus for planning a surgical method for treating the cranial base to mandibular axis discrepancies in a patient comprising an artificial jaw simulator including an upper member with a downwardly facing surface and having a pair of spaced sockets at one end, which represent the sockets of the patient's glenoid fossae, pivotally mounted on a pair of spaced spherical styluses, which represent the simulated horizontal or hinge axis of the patient's condyles, on a frame vertically mounted on one end of a lower member with an upwardly facing surface, and a model of an upper dental arch of the patient with a base, which is parallel on all sides to the upper dental arch model and is delineated with horizontal and vertical reference lines, mounted with a separating media to a mounting stone mounted on an upper plate which is mounted to the downwardly facing surface of the upper member of the artificial jaw simulator, and a model of a lower dental arch of the patient mounted on a mounting stone, which is parallel on all sides to the lower dental arch model and is delineated with horizontal and vertical reference lines, mounted using a settable material on a lower plate which is mounted to the upwardly facing surface of the lower member of the artificial jaw simulator, wherein the relative motion between the upper and lower plates with the models mounted thereon is the same as the relative motion between the patient's upper and lower jaws, and wherein the true axis of rotation of the temporomandibular joints of the patient have been maintained.

The present invention further provides an orthotic for stabilizing the condylar positions in the temporomandibular joints of a patient with temporomandibular dysfunction syndrome comprising a base portion with an upper and a lower surface, an anterior and posterior surface, and having a generally U-shaped plan form and including opposite integrally formed side arms adapted for location between the orthotic and mandibular teeth of the patient, the base having an inner flange along its trailing edge and an outer flange along its leading edge wherein the inner flange and outer flange extend upward from the base so as to form a channel for accepting the maxillary teeth of the patient wherein the bottom surfaces of the maxillary teeth are in contact with the surface of the channel, and wherein the width of the channel is adapted to the width of the maxillary teeth of the patient, and wherein the base has a vertical thickness sufficient that when the maxillary teeth are engaged in the orthotic there is complete disclusion of the posterior maxillary and mandibular teeth during eccentric jaw movements, and wherein the thickness of the base in the position where the anterior maxillary teeth are engaged defines a downwardly extending ramp with anterior and posterior surfaces of sufficient thickness to allow the superior surface of the central and lateral incisors to glide freely along the posterior surface of the ramp to simulate the guidance of normal central and lateral incisors against the lingual surface of normal anterior maxillary teeth in a condition of no wear and normal vertical anatomy and to provide anterior guidance of the patient's mandible in excursive movements by contact of the superior surface of the central and lateral incisors with the posterior surface of the ramp so as place the posterior maxillary and mandibular teeth out of contact.

The present invention further provides an orthotic for maintaining the mandible to maxilla/cranial base alignment and stability in the temporomandibular joints of a patient during or following a surgery which verifies stable condylar position in the temporomandibular joints of the patient comprising a base portion having a generally U-shaped plan form and including opposite integrally formed side arms adapted for location between the maxillary and mandibular teeth of the patient, the base having an inner flange along its trailing edge and an outer flange along its leading edge and extending upward and downward from the base so as to form an upper channel for accepting the maxillary teeth and a lower channel for accepting the mandibular teeth of the patient and which when fitted to the patient's teeth maintains the mandible to maxilla/cranial base alignment and stability in the temporomandibular joints of the patient.

Objects

It is an object of the present invention to provide a method for treating maxilla/cranial base to mandibular axis discrepancies in the temporomandibular joints of a patient such as is caused by MTDS or developmental facial/dental deformities without performing open jaw joint surgery.

It is a further object of the present invention to provide a method for treating maxilla/cranial base to mandibular axis discrepancies in the temporomandibular joints of a patient such as caused by MTDS or developmental facial/dental deformities by performing total maxillary osteotomy either alone or in conjunction with mandibular osteotomy.

It is a further still object of the present invention to provide a method for treating maxilla/cranial base to mandibular axis discrepancies in the temporomandibular joints of a patient such as those caused by MTDS or developmental facial/dental deformities wherein the surgical procedure for treating is planned on a model of the patient's mouth wherein the true axis of rotation of the patient's jaw joint in a stable condylar position has been replicated.

These and other objects of the present invention will become increasingly apparent with reference to the following drawings and preferred embodiments.

DETAILED DESCRIPTION OF THE INVENTION

Figure 1:
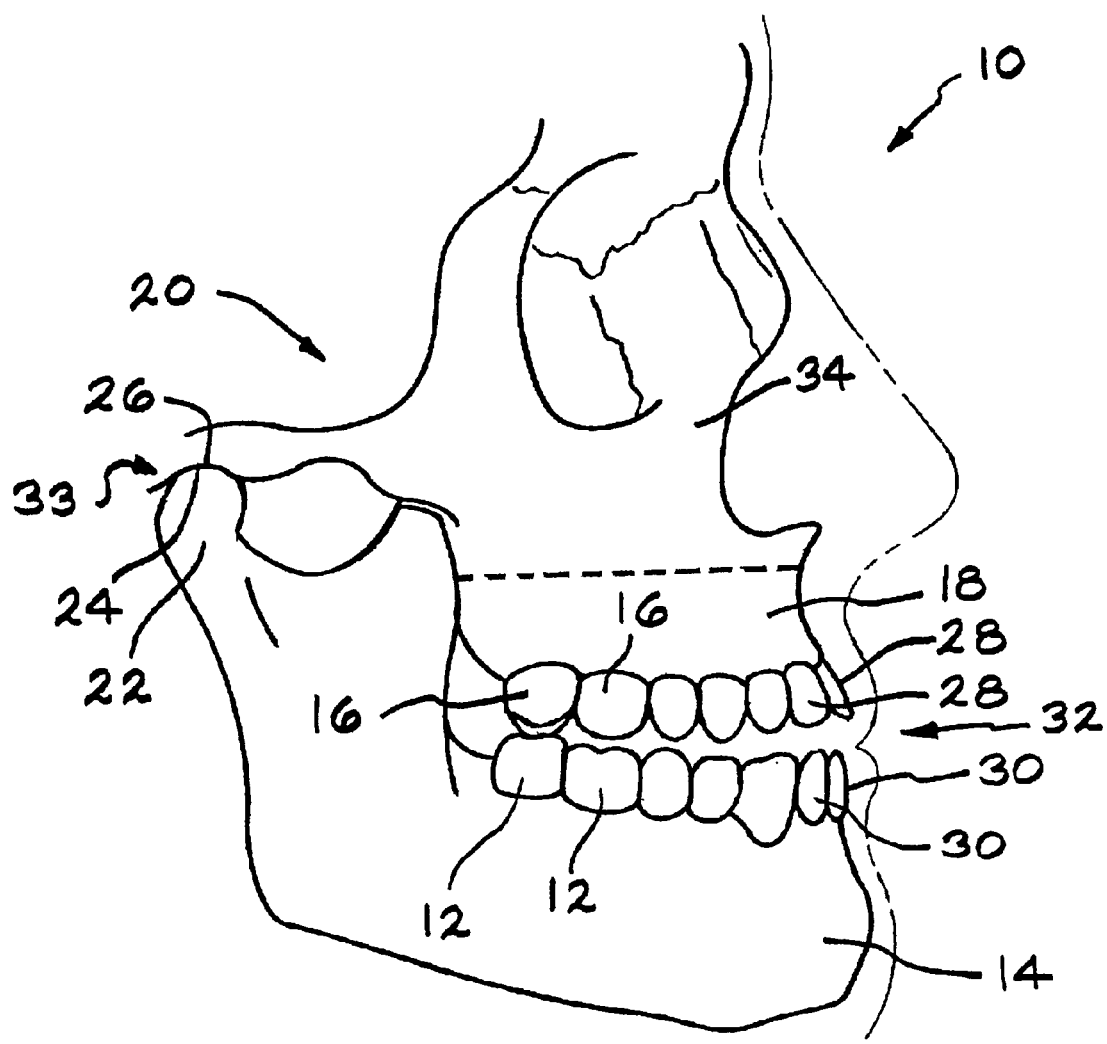
FIG. 1 illustrates schematically a side view of a part of the skull 34, maxilla 18, and mandible 14 of a particular patient 10 that has MTDS. The dotted line indicates where the maxilla 18 is to be surgically cut to enable the maxilla 18 to be disarticulated from the skull 34 during total maxillary osteotomy.

All patents, patent applications, government publications, government regulations, and literature references cited in this specification are hereby incorporated herein by reference in their entirety. In case of conflict, the present description, including definitions, will control.

The present invention provides a method for surgically treating maxilla/cranial base to mandibular axis discrepancies in the temporomandibular joints of a patient such as caused by mandibular, temporomandibular dysfunction syndrome (MTDS) or developmental facial/dental deformities wherein the maxillary teeth are out of alignment with the mandibular teeth and wherein the misalignment is caused by one or more defects in the structural arrangement of the patient's upper jaw (maxilla) to the patient's lower jaw (mandible).

For example, if the patient's anterior maxillary teeth do not overlap the anterior mandibular teeth (central and lateral incisors) when the patient's mouth is in the closed position, the patient's mandible can be pushed forward with the posterior mandible going downward and backward, particularly if the patient's posterior maxillary and mandibular teeth are in contact. The misalignment destabilizes the patient's jaw joint: the mandibular condyles are not stably positioned in their respective sockets of the glenoid fossa (jaw joint) and as the patient opens and closes his mouth, the condyles rotate and translate inappropriately in and out of their sockets. Because the patient's jaw is not in its stable condylar position, the ligaments in the jaw joint become stretched, endema and/or inflamation of the jaw joint usually occur, and the patient experiences problems of sustained muscle contractions and related spasms and internal derangement of the jaw joint meniscus/disc. As a consequence, the patient cannot maintain a functional bite and depending on the degree of jaw joint instability, the patient can experience severe and persistent pain and/or severe headaches, ear aches, neck and shoulder pain, and tinnitus.

The present invention provides a method for treating maxilla/cranial base to mandibular axis discrepancies in the temporomandibular joints of a patient such as is caused by TMDS or developmental facial/dental deformities for realigning the maxilla in relationship to the mandible such that the realigned maxilla and mandible maintain each condyle in a stable position in its socket of the glenoid fossa, which restores a functional bite to the patient. The resolution and treatment is achieved by orthognathic surgery (corrective jaw surgery) which includes total maxillary osteotomy with or without mandibular osteotomy to restore a functional bite to the patient.

Hereinafter, the term "surgical procedure" refers to orthognathic surgery which includes total maxillary osteotomy, mandibular osteotomy, or both.

The term "functional bite" refers to an appropriate bite wherein the teeth are in a skeletal and dental Class I relationship, with the jaw joint in a stable condylar position with appropriate anterior guidance.

The term "treating" includes managing or correcting.

The novel features of the method are that (1) a craniomandibular orthopedic repositioning orthotic is used to deprogram over time a patient's jaw into a stable condylar position wherein each mandibular condyle is stabilized in its socket of the glenoid fossa (stable condylar position), which then enables the patient's jaw joint true hinge axis to be measured, (2) the surgical procedure for treating, managing, or correcting maxilla/cranial base to mandibular axis discrepancies in the temporomandibular joints of a patient such as is caused by MTDS or developmental facial/dental deformities in the patient is planned on a model of the patient's mouth in which the patient's true hinge axis in the stable condylar position has been replicated, and (3) the surgical procedure uses total maxillary osteotomy, with or without mandibular osteotomy, to treat, manage, or correct the maxilla/cranial base to mandibular axis discrepancies in the temporomandibular joints of a patient such as is caused by MTDS or developmental facial/dental deformities. A further novel feature of the present invention is that the method provides for the treatment, management, or correction of maxilla/cranial base to mandibular axis discrepancies in the temporomandibular joints of a patient such as is caused by MTDS or developmental facial/dental deformities without involving surgery on the temporomandibular joint itself. In other words, the method of the present invention enables a surgical procedure to be planned, which instead of relying on open or closed jaw joint surgery to treat, manage, or correct maxilla/cranial base to mandibular axis discrepancies in the temporomandibular joints of a patient such as is caused by MTDS or developmental facial/dental deformities, uses total maxillary osteotomy, mandibular osteotomy, or both.

The method of the present invention, which provides a means for treating, managing, or correcting maxilla/cranial base to mandibular axis discrepancies in the temporomandibular joints of a patient such as caused by MTDS or developmental facial/dental deformities, comprises the following four steps.

(1) Stabilizing over time the mandible in relation to the cranial base, i.e., stabilizing each condyle in its socket of the glenoid fossa over time, by using a craniomandibular orthopedic repositioning orthotic which is applied to the maxillary teeth (dentition) of the patient so as to allow full coverage of all the teeth. The function of the orthotic is to over time allow the mandible to realign to the cranial base in the patient and to restore the facial muscles to their proper physiologic resting length by removing the neural inputs of the teeth to the brain in determining the position of the mandible in relation to the cranium. When the orthotic is applied to the maxillary teeth, the primary determinant of mandible position is provided by the orthotic and neural inputs from the temporomandibular joint to the brain and not the neural inputs of the teeth. Removing the neural inputs of the teeth reduces problems of sustained muscle contraction and related spasm and joint inflamation which enables each condyle over time to become stabilized in its socket of the glenoid fossa, thus stabilizing dislocation of the articular disc. After the patient's condyles have been stabilized in their sockets of the glenoid fossa (stable condylar position), the jaw joint is in its true hinge axis of rotation and healing of the jaw joint occurs.

(2) Replicating the patients' jaw joint true hinge axes of rotation in the stabilized condylar position on an artificial jaw simulator (articulator) containing plaster casts of the upper and lower dental arches of the patient mounted thereon. It is important that the mounting plaster casts of the patient's upper and lower dental arches on the articulator is performed in such a manner so as to transfer the true axis of rotation of each jaw joint from the patient to the articulator while maintaining the stable condylar position in each jaw joint. By transferring the true axis of rotation of the patient's jaw joints, a surgical procedure can be accurately planned to treat, manage, or correct vertical jaw discrepancies causing MTDS or which are a result of developmental facial/dental deformities. Articulators have been disclosed in U.S. Pat. No. 4,034,475 to Lee, U.S. Pat. No. Re. 31,615 to Lee, and U.S. Pat. No. 4,909,737 to Lee. However, the preferred articulator is that disclosed in U.S. Pat. No. 6,109,917 to Lee et al. and which is commercially available from Panadent Corporation, Grand Terrace, Calif.

(3) Planning the surgical procedure (total maxillary osteotomy with or without mandibular osteotomy) on the articulator with the patient's dental arch casts mounted thereon wherein the surgical procedure for correcting the maxilla/cranial base to mandibular axis discrepancies in the temporomandibular joints of a patient such as caused by MTDS or developmental facial/dental deformities reapproximates the patient's maxillary and mandibular teeth into a position coincidental to the stabilized jaw joint position with a functional bite which at the same time maintains the jaw joint in a stable condylar position. The articulator with the patient's dental arch casts mounted thereon is also used to design and construct surgical stints to serve as guides for relating the maxilla to the mandible during the surgery.

(4) Performing the surgical procedure on the patient based on the surgical procedure planned on the artificial jaw simulator with the patient's dental arch casts mounted thereon to treat, manage, or correct the maxilla/cranial base to mandibular axis discrepancies in the temporomandibular joints of a patient such as caused by MTDS or developmental facial/dental deformities of the patient wherein the surgical procedure reapproximates the patient's maxillary and mandibular teeth into a functional bite while at the same time maintaining the stable condylar position in the jaw joint.

Figure 2:
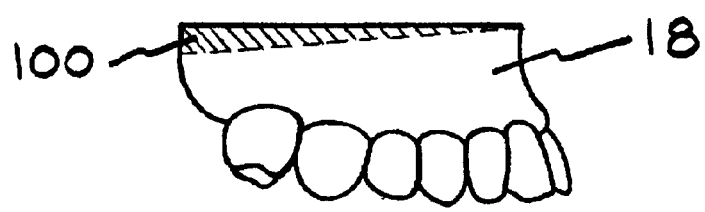
FIG. 2 illustrates schematically the maxilla 18 disarticulated from the skull 34 of the patient 10 shown in FIG. 1. The shaded portion 100 illustrates the amount of maxillary bone to be removed to restore a functional bite to the patient 10 in FIG. 1.
Figure 3:
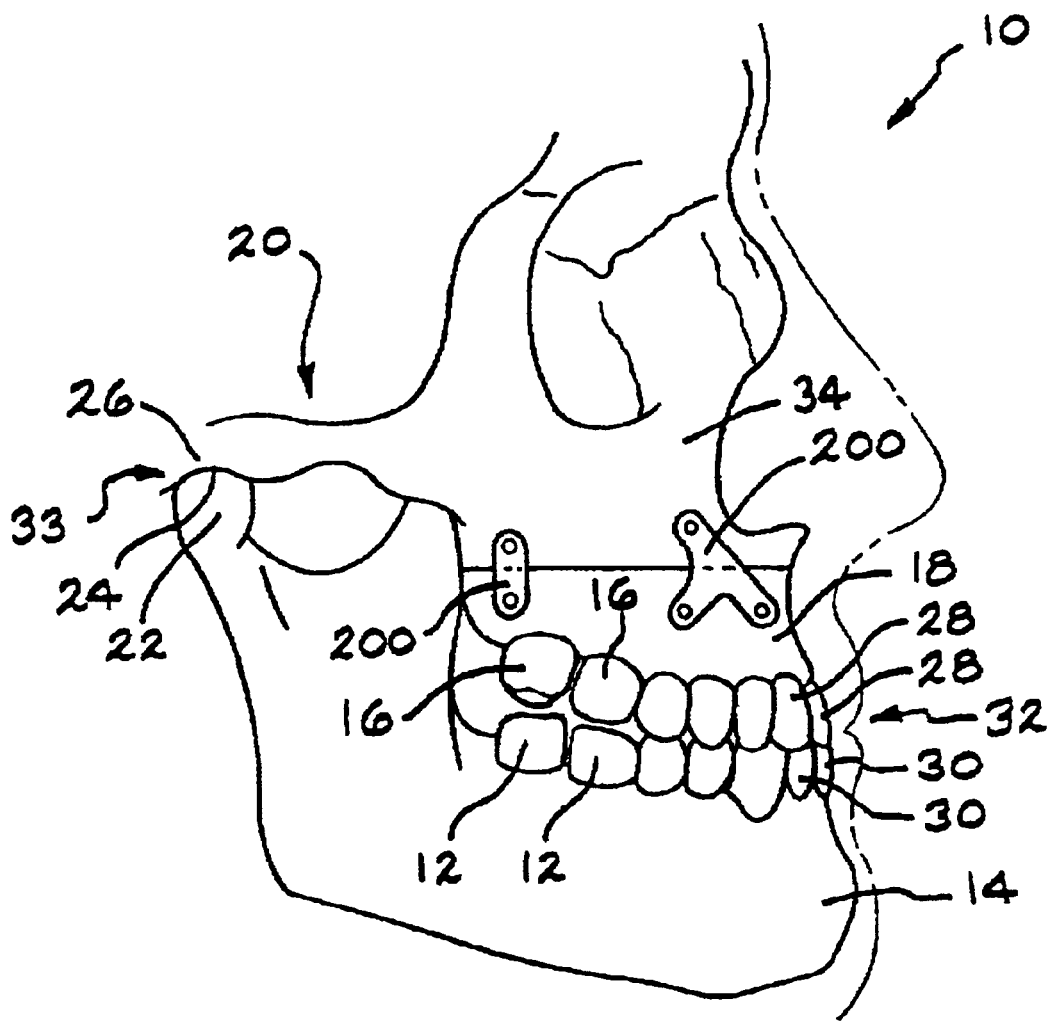
FIG. 3 illustrates schematically a side view of a part of the skull 34, maxilla 18, and mandible 14 of the patient 10 shown in FIG. 1 after total maxillary osteotomy to restore the functional bite to the patient 10.

FIGS. 1, 2, and 3 illustrate the basic principle of jaw realignment using total maxillary osteotomy in a surgical procedure for treating, managing, or correcting maxilla/cranial base to mandibular axis discrepancies in the temporomandibular joints of a patient such as caused by MTDS or developmental facial/dental deformities in a patient wherein the surgical procedure had been planned on a model which replicates the patient's jaw joint in a stable condylar position as determined by the prior step of deprogramming the patient's jaw into the stable condylar position with a craniomandibular orthopedic repositioning orthotic. The fundamentals of total maxillary osteotomy (often referred to as Le Fort I) are standard and have been described in many texts on surgical techniques, for example in the text by Kelly in *Atlas of Oral and Maxillofacial Surgery* (Keith ed., W. B. Saunders Company, Philadelphia, (1992) pp. 73–86).

FIG. 1 shows the jaw alignment of a particular patient 10 with a discrepancy caused by MTDS. In the figure, the posterior mandibular teeth 12 on the mandible 14 are in contact with the posterior maxillary teeth 16 on the maxilla 18. As a result of the contact of the posterior mandibular teeth 12 and the posterior maxillary teeth 16 and the neural inputs from the contact, the mandible 14 in relation to the cranial base 20 is destabilized. In particular, the condyle 22 on the mandible 14 is not stably positioned in the socket 24 being positioned inferiorly and posteriorly of the glenoid fossa 26, i.e., the temporomandibular joint (jaw joint) 33. Further, as shown in the figure, the anterior maxillary teeth 28 are not properly positioned to be anterior to and overlap the mandibular anterior teeth (central and lateral incisors) 30 thereby providing anterior guidance.

In a normal person, the anterior maxillary teeth 28 overlap the anterior mandibular teeth 30 which during opening and closing of the mouth 32 the anterior maxillary teeth 28 propreoceptively guides the position of the mandible 14 thereby maintaining a stable condylar position, i.e., each condyle 22 is in a stable position in its socket 24 of the glenoid fossa 26 at the maxilla/cranial base 20. However, in a patient with MTDS, the anterior maxillary teeth 28 are unable to act as a guide when the mouth 32 is opened or closed in maintaining the condyle 22 in a stable position in the socket 24 of the glenoid fossa 26. As a result, in a patient with severe MTDS, the pressure on the posterior teeth (16 and 12), which causes the condyle 22 to be pulled from the socket 24 as the jaw joint 33 is closed, causes pain to the patient. In milder MTDS cases, the jaw joint 33 makes a clicking sound as the condyle 22 slips in and out of position with the articular disc (not shown) in the socket 24 when the mouth 32 is opened and closed. Traditional attempts to treat, manage, or correct maxilla/cranial base 20 to mandible 14 axis discrepancies in the jaw joint 33 of a patient such as is caused by MTDS or facial/dental deformities involved surgery on the jaw joint 33 without taking into consideration the role the relationship of the maxillary anterior teeth 28 to the mandibular anterior teeth (central and lateral incisors) 30 and the jaw joint 33 in a stable condylar position, for example see Keith in *Atlas of Oral and Maxillofacial Surgery* (Keith ed., W. B. Saunders Company, Philadelphia, (1992) pp. 201–216). Therefore, jaw joint surgery provides only a temporary respite because over time, the patient's mandible 14 relationship to the maxilla/cranial base 20 eventually becomes destabilized and the discrepancies remanifest.

The surgical procedure in the method of the present invention treats, manages, or corrects maxilla/cranial base 20 to mandible 14 axis discrepancies in the jaw joints 33 of a patient such as is caused by MTDS or facial/dental deformities by repositioning the mandible 14 and mandibular anterior teeth (30) with respect to the maxilla (18) and maxillary anterior teeth (28) so as to stabilize the condyle 22 in the socket 24 of the glenoid fossa 26 which stabilizes the mandible 14 relationship to the cranial base 20. First, a stable condylar position is induced over time by the use of a craniomandibular orthopedic repositioning orthotic, which is worn continuously by the patient for a time sufficient to deprogram the jaw joint 33 into the stable condylar position with subsequent healing of the jaw joint 33, and the surgical procedure to reposition the maxilla 18 is planned on a model of the patient's jaw in the stable condylar position induced by the orthotic. To reposition the maxilla (18) and maxillary teeth (16 and 28) with respect to the mandible (14) and mandibular teeth (12 and 30), the maxilla 18 is surgically cut along a transverse (horizontal) line (dotted line shown in FIG. 1) and the maxilla 18 disarticulated from the remainder of the patient's skull 34.

FIG. 2 shows the disarticulated maxilla 18. The figure shows the amount of maxillary bone for the illustrated patient of FIG. 1 that is to be removed 100 in order to place the patient's maxillary teeth (16 and 28) in a position that maintains the stable condylar position in the patient when the disarticulated maxilla 18 is reattached to the patient's skull 34 as shown in FIG. 3. In general, the effect of the bone removal 100 is that when the maxilla 18 is reattached to the skull 34, the posterior maxillary teeth 16 are elevated with respect to their position prior to surgery and in some cases, the anterior maxillary teeth 28 are also lowered with respect to their position prior to surgery.

FIG. 3 shows the particular patient 10 after the maxilla 18 has been repositioned by surgery. In the figure, the maxilla 18 with the amount of bone-removed as shown in FIG. 2 has been reattached to the patient's skull 34. Preferably, surgical plates 200 are used to keep the maxilla 18 reattached to the skull 34 and to facilitate healing of the maxilla 18 and skull 34 across the cut. As shown in the Figure, when the patient's mouth 32 is in the closed position, the anterior maxillary teeth 28 are now anterior to and partially overlap the anterior mandibular teeth (central and lateral incisors) 30 and the posterior maxillary teeth 16 are not in contact with the posterior mandibular teeth 12. Because of the guidance provided by the anterior maxillary teeth 28 and the lack of contact between the posterior maxillary teeth 16 and the posterior mandibular teeth 12, the condyle 22 is maintained in its stable position in the socket 24 of the glenoid fossa 26 comprising the jaw joint 33 which stabilizes the mandible 14 in a stable relationship to the cranial base 20.

Thus, FIGS. 1, 2, and 3 illustrate the basic surgical procedure comprising total maxillary osteotomy for treating, managing, or correcting maxilla/cranial base to mandibular axis discrepancies in the temporomandibular joints of a patient such as caused by MTDS or developmental facial/dental deformities. However, in particular cases the surgical procedure can further include mandibular osteotomy. The surgical procedure can further include widening or narrowing the maxilla or widening or narrowing the mandible so as to place the maxillary teeth in a stable lateral relationship over the mandibular teeth. The surgical procedure can further include retruding or advancing the maxilla or mandible with respect to each other so as to minimize deharmonizing effects on facial soft and hard tissue.

The craniomandibular orthopedic repositioning orthotic is an important element in the method of the present invention. The orthotic is designed to place the patient's mandible in a stable relationship with the cranial base by removing the neural inputs from the teeth which enables the jaw joint over time to be deprogrammed into a stable condylar position. The design of the orthotic further includes an anterior ramp with a posterior surface defining an anterior guide plane and an anterior surface. The anterior ramp enables the orthotic to provide anterior guidance of the mandible in excursive movements by contact of the superior surface of the anterior mandibular teeth against the posterior surface the anterior ramp of the orthotic. The anterior guide plane of the orthotic is designed to allow for complete disclusion of the posterior teeth during eccentric jaw movements, i.e., protrusive, right, and left lateral positioning.

In the protrusive position, the superior surface of the anterior mandibular teeth (central and lateral incisors) contact the posterior surface of the anterior ramp only, with all posterior maxillary teeth and posterior mandibular teeth about 5 mm out of contact. In right and left lateral excursive movements, the anterior guide plane of the maxillary orthotic allows the mandibular cuspid (canine) teeth to guide the mandible to disclusion of the maxillary and mandibular posterior teeth. The anterior guide plane of the anterior ramp is designed to be passive in its affect on mandibular position. Because the anterior guide plane of the anterior ramp is designed to be passive in its effect, it allows the mandibular anterior teeth (central and lateral incisors) to glide freely along the posterior surface of the anterior ramp, which simulates the guidance of normal anterior mandibular teeth (central and lateral incisors) against anterior maxillary teeth in a condition of no wear and normal vertical anatomy.

Figure 5A:
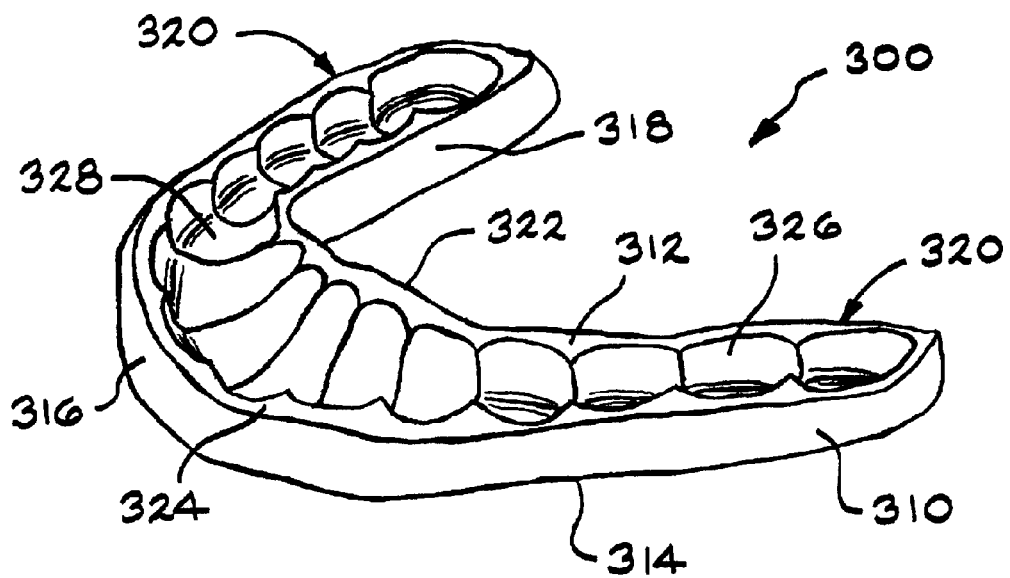
FIG. 5A is a perspective view of the upper side of a craniomandibular orthopedic repositioning orthotic 300 for deprogramming a patient's jaw into a stable condylar position.
Figure 5B:
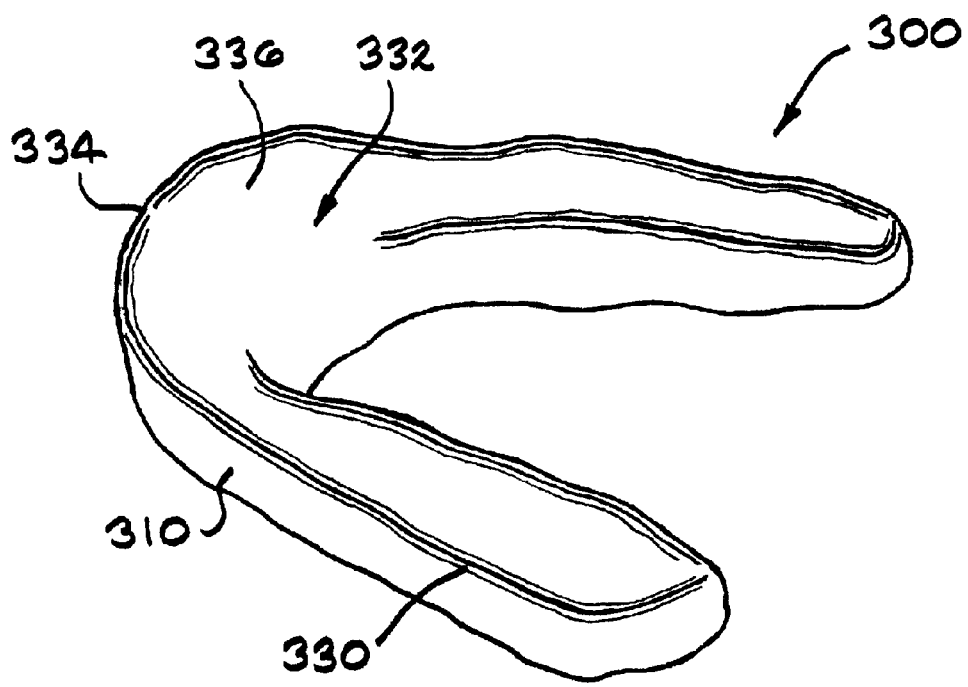
FIG. 5B is a perspective view of the underside of the orthotic 300 of FIG. 5A.

FIGS. 5A and 5B illustrate a craniomandibular orthopedic repositioning orthotic for deprogramming the jaw joint into a stable condylar position. FIG. 5A shows an above perspective view of the orthotic 300 with a base portion 310 with an upper surface 312 and a lower surface 314, an anterior surface 316 and posterior surface 318, and having a generally parabolic or U-shaped plan form and including opposite integrally formed side arms 320 adapted for location between the maxillary and mandibular teeth of the patient. The base 310 has an inner flange 322 along its trailing edge and an outer flange 324 along its leading edge wherein the inner flange 322 and outer flange 324 extend upward from the base 310 so as to form a channel 326 for accepting the maxillary teeth of the patient wherein the bottom surfaces of the maxillary teeth are in contact with the surface 328 of the channel 326. The orthotic 300 is specially designed for each patient so that the width of the channel 326 is adapted to the width of the maxillary teeth of the patient and the ramp is of a length sufficient to provide a guide plane which allows for complete disclusion of the posterior maxillary teeth and posterior mandibular teeth during eccentric jaw movements.

FIG. 5B shows a bottom perspective view of the orthotic 300. The base 310 has a vertical thickness 330 sufficient that when the maxillary teeth are engaged in the orthotic 300 there is complete disclusion of the upper and lower posterior teeth during eccentric jaw movements. Also shown is the anterior ramp 332 wherein the thickness of the base 310 in the position where the anterior maxillary teeth (central and lateral incisors) are engaged defines a downwardly extending anterior ramp 332 with an anterior surface 334 and a posterior surface 336 of sufficient thickness to allow the superior surface of the anterior mandibular teeth (central and lateral incisors) to glide freely along the posterior surface 336 of the anterior ramp 332 to simulate the guidance of normal anterior mandibular teeth (central and lateral incisors) against normal anterior maxillary teeth in a condition of no wear and normal vertical anatomy and wherein in a protrusive position the superior surface of the anterior mandibular teeth (central and lateral incisors) contact the posterior surface 336 of the anterior ramp 332 and the posterior maxillary teeth and posterior mandibular teeth are placed out of contact.

Deprogramming the jaw joint into a stable position using the orthotic entails an adjustment process which can extend over a period of time. The goal of the adjustment process is to eliminate all posterior contacts in lateral excursions on the posterior of the orthotic while allowing the condyles to passively seat to a stable position in their respective sockets of the glenoid fossa. During the adjustment process, the patient is required to wear the orthotic 24 hours a day, seven days a week except when it is removed for cleaning. When the orthotic is removed for cleaning, the teeth should not be allowed to come into contact. As the adjustment process proceeds, it will become necessary to remove acrylic from the posterior of the orthotic in order for the condyles to reach their stable position in their sockets while maintaining complete disclusion of the posterior maxillary and mandibular teeth during eccentric jaw movements. For some patients, as the adjustment process proceeds, in addition to removing acrylic from the posterior of the orthotic, it can become necessary to add acrylic to the anterior ramp of the orthotic to extend the anterior guide plane to maintain proper guidance. Alternatively, orthotics are sequentially fitted to the patient wherein the posterior of each orthotic in the sequence has been progressively decreased in thickness and where appropriate, the anterior ramp of each orthotic in the sequence has been progressively elongated to extend the anterior guide plane.

The time of the adjustment process for deprogramming the patient's jaw into a stable condylar position and the number of adjustments that may be needed to enable the patient's jaw to deprogram into a stable condylar position will vary from patient to patient. However, for all patients, determining when the jaw is in its final stable condylar position is when all three of the following stable condylar position criteria are satisfied.

First, the patient is pain free and has a consistently reproducible bite on the orthotic.

Second, there is complete neuromuscular release whereby the muscles upon palpation show no signs of guarding, splinting, or tension to the palpation or application of bimanual manipulation procedures on the mandible by the operator (bimanual manipulation procedures are described in Dawson, a treatise well known to those skilled in the art).

Figure 4A:
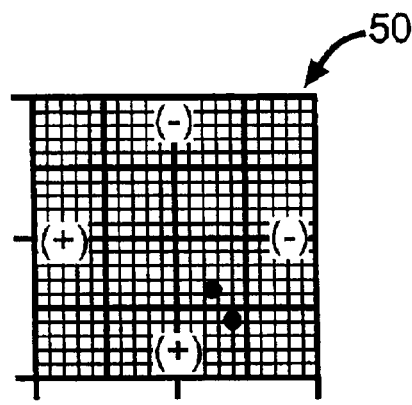
FIG. 4A shows a graph 50 of a measurement of a patient's left jaw joint C.P.I. using a Panadent C.P.I. apparatus showing that the dots, each representing the condylar position of the patient recorded at a particular time, produces a C.P.I. of greater than about 1 mm indicating that the patient's condylar position has not reached stability.
Figure 4B:
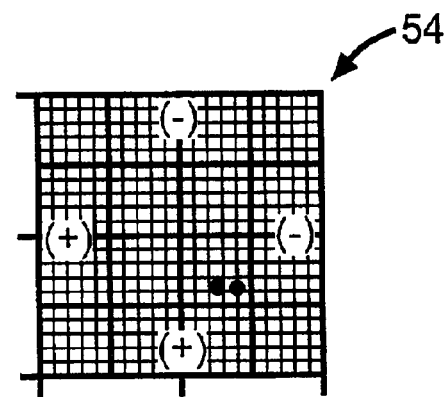
FIG. 4B shows a graph 54 of a measurement of a patient's left jaw joint C.P.I. using a Panadent C.P.I. apparatus showing that the dots, each representing the condylar position of the patient recorded at a particular time, produces a C.P.I. of about 1 mm indicating that the patient's condylar position has been stabilized.

Third, the patient has a condylar position index (C.P.I.) of less than about 1 mm using a commercially available Panadent C.P.I. apparatus such as the CPI-III-H (Panadent Corporation, Grand Terrace, Calif.) or equivalent containing models of the patient's upper and lower dental arches mounted therein with the patient's orthotic fitted on the teeth of the upper dental arch for measuring condylar positions in a patient during opening and closing of the model of the patient's mouth. A condylar position index of less than about 1 mm means that the difference between the position of the condyle within the socket when the jaw is closed with the teeth in contact and the position it is in the stable condylar position is less than about 1 mm. FIG. 4A shows a graph 50 of a measurement of a patient's left jaw joint C.P.I. using a Panadent C.P.I. apparatus showing that the dots, each representing the condylar position of the patient recorded at a particular time, produces a C.P.I. of greater than about 1 mm indicating that the patient's condylar position has not reached stability. FIG. 4B shows a graph 54 of a measurement of a patient's left jaw joint C.P.I. using a Panadent C.P.I. apparatus showing that the dots, each representing the condylar position of the patient recorded at a particular time, produces a C.P.I. of about 1 mm indicating that the patient's condylar position has been stabilized.

Figure 4C:
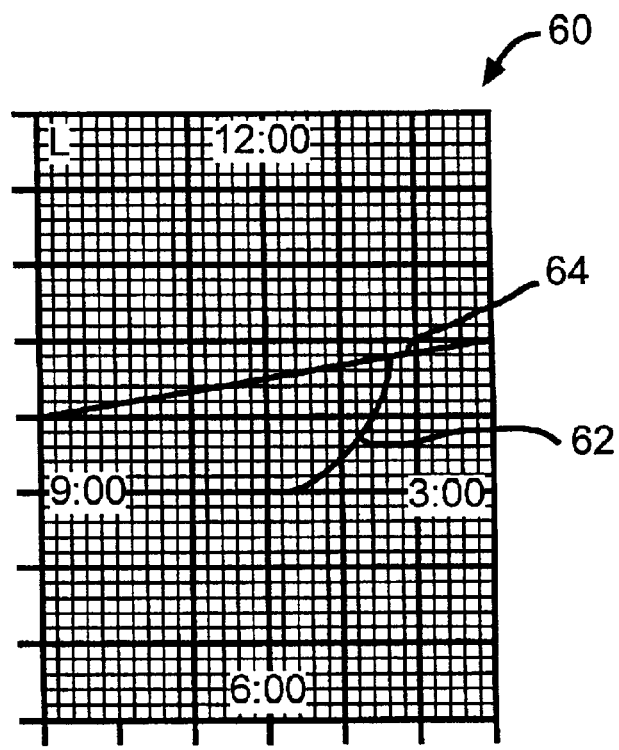
FIG. 4C shows a graph 60 of a measurement of a patient's condylar true hinge axis and condylar pathway of the patient's left jaw joint using a condylar axis tracking apparatus.

After the patient's jaw has been deprogrammed and the patient's C.P.I. is less than about 1 mm, the condylar true hinge axis of rotation and condylar pathway of each jaw joint (axes of rotation and shape of the patient's sockets) are determined using codylar axis tracking apparatus disclosed in U.S. Pat. No. Re. 31,615 to Lee or other condylar tracking apparatus well known in the art such as the commercially available AXI-PATH recorder available from the Panadent Corporation. The shape of the patient's sockets and true hinge axis of rotation are transferred to the artificial jaw articulator (FIGS. 7 to 9) which is used for planning the surgical procedure to treat, manage, or correct vertical jaw discrepancies causing MTDS or which are a result of developmental facial/dental deformities. FIG. 4C shows a graph 60 of a measurement of a patient's condylar true hinge axis and condylar pathway of the patient's left jaw joint using a condylar axis tracking apparatus. Line 62 traces the path of the condyle in the socket as the patient's mouth opens. Where line 62 intersects line 64 is the position of the condyle when the patient's mouth is closed. The angle between lines 62 and 64 is the patient's condylar true hinge axis.

The stable condylar position criteria must be met before patient's jaw relationship, i.e., true hinge axis of rotation, can be transferred to an artificial jaw simulator comprising a model of the patient's mouth. A comprehensive understanding of orthotic fabrication, adjustment, C.P.I. measurements as well true hinge axis determinations and transfers is known to those in the art and can be obtained by the level I and II courses taught by Orognathic Bioesthetics International, Salem, Oreg. Preferably, the patient has worn the orthotic for a time sufficient for healing of the jaw joint to occur which includes tightening of the ligaments in the jaw joint and cessation of endema and/or jaw joint inflammation.

Once the patient has undergone the adjustment process and the patient's jaw joint has been stabilized as determined by satisfaction of the stable condylar position criteria, the surgical procedure for treating, managing, or correcting the maxilla/cranial base to mandibular axis discrepancies is planned. The surgical procedure is planned on a model of the patient's mouth which comprises an artificial jaw simulator with casts of the patient's maxillary and mandibular dental arches mounted thereon wherein model replicates the patient's true hinge axis of rotation determined with the condylar axis tracking apparatus as follows.

Dental arch casts of the patients upper (maxillary) and lower (mandibular) dental arches are fabricated in dental stone. The upper dental arch cast includes a base about 10 thick and parallel on all sides. The dental arch casts are split cast mounted to bases on the articulator. In the appropriate mounting stone on the artificial jaw simulator; the lower dental arch cast is mounted to the lower mounting plate and the upper dental arch cast is mounted to the upper mounting plate with the sides of the upper dental arch cast base parallel and confluent to the upper mounting plate. Prior to mounting the upper dental arch cast, a separating media is placed between the base of the upper dental arch cast and the upper mounting stone. Horizontal reference lines are scored into the base of the upper dental arch cast delineating 5 and 10 mm of vertical height on the base and vertical lines are scored to traverse the base and upper mounting stone at three positions around the casts: right and left posterior and midline anterior. The horizontal and vertical reference lines enable the amount of maxillary bone to be removed during surgery to be determined.

Figure 6:
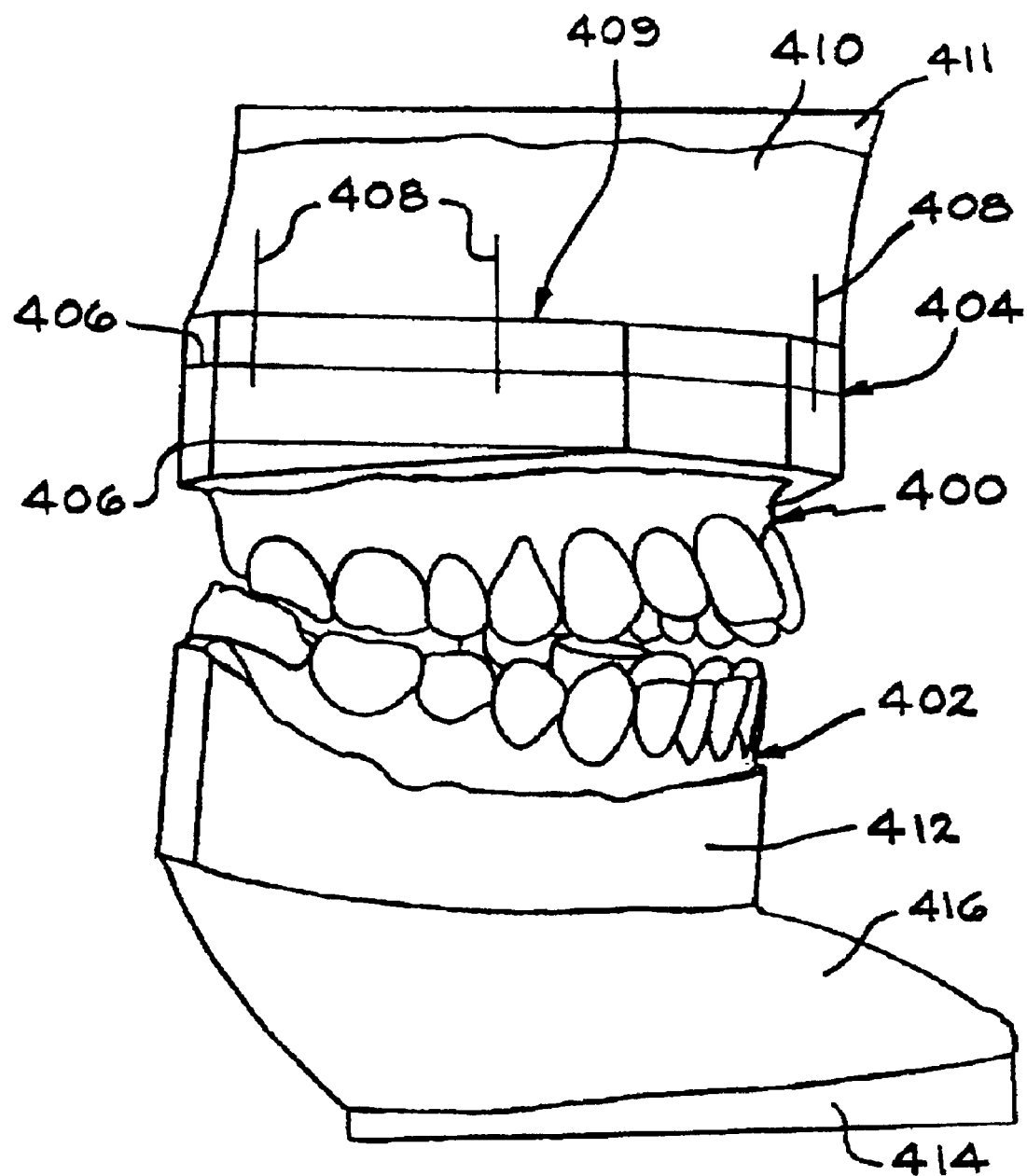
FIG. 6 is a perspective view of the upper dental arch 400 and lower dental arch 402 of a particular patient with MTDS.

FIG. 6 illustrates upper and lower dental arch casts made from a patient with MTDS. The Figure shows upper dental arch cast 400 and lower dental arch cast 402. The upper dental arch cast 400 is mounted on a base 404. The base 404 with upper dental arch 400 mounted thereon is mounted to the upper mounting stone 410 with upper mounting plate 411 using separating media (not shown) which enables the base 404 to be easily mounted or dismounted. The base 404 has scored thereon horizontal reference lines 406 and vertical reference lines 408. The vertical reference lines 408 traverse the junction 409 between the base 404 and the upper mounting stone 410. The lower dental arch 402 and lower mounting stone 412 is mounted to lower mounting plate 414 using settable material 416 (e.g., plaster).

Figure 7:
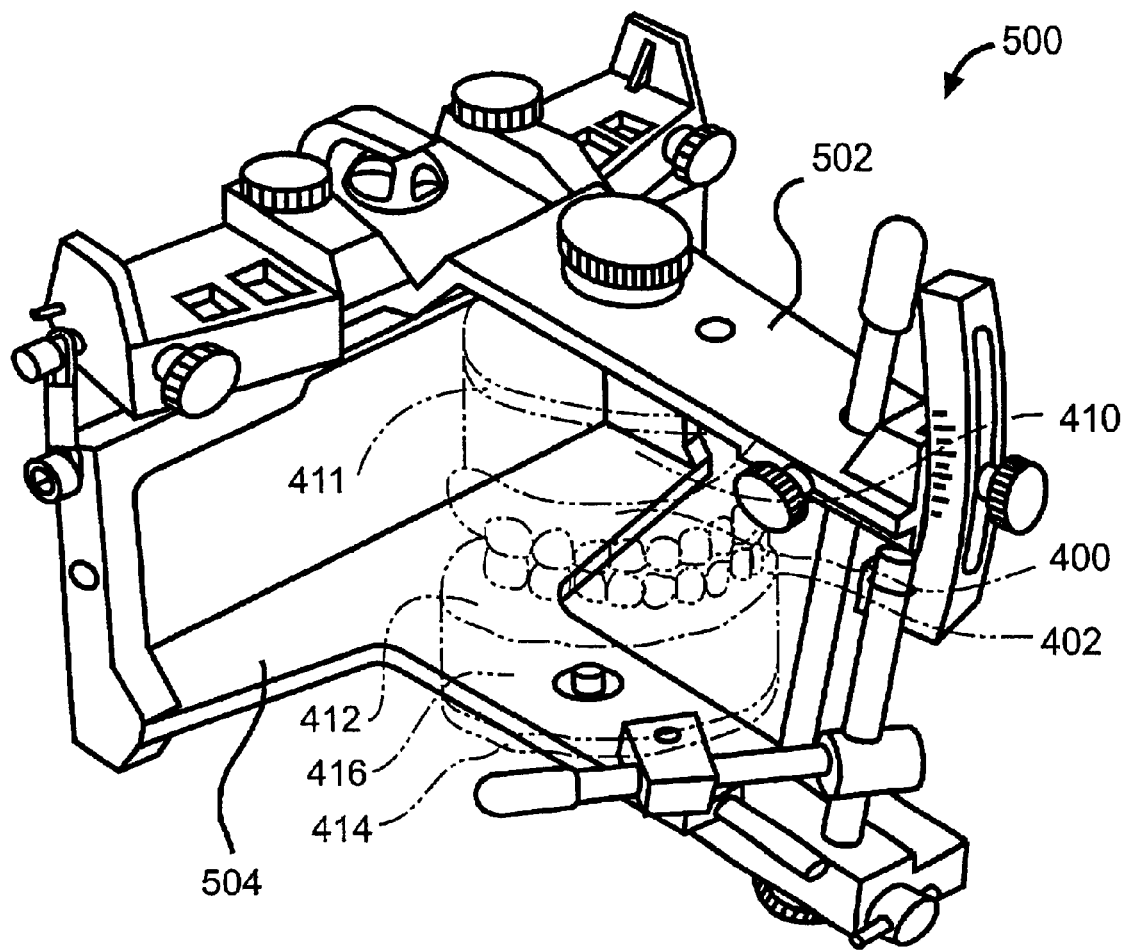
FIG. 7 is a perspective view of a preferred prior art artificial jaw simulator 500.

FIG. 7 shows a perspective view of an artificial jaw simulator 500 as disclosed in U.S. Pat. No. Re. 31,615 to Lee which is suitable for planning the surgical procedures. The Figure shows artificial jaw simulator 500 with upper member 502 with upper mounting plate 411 and stone 410 comprising upper dental arch 400 mounted thereon and lower member 504 with the lower mounting plate 414 and stone 412 comprising lower dental arch 402 mounted thereon. Other artificial jaw simulators which enable the patient's true hinge axis and a stable condylar position to be replicated can be used for planning the surgical procedure.

With the dental arch casts mounted in the artificial jaw simulator in the patient's true hinge axis and in a stable condylar position in a split cast fashion, the upper dental arch cast is then disarticulated from the upper mounting plate and stone. The upper dental arch cast is related to the lower dental arch cast, which is still mounted to the lower mounting plate and stone of the artificial jaw simulator, in a skeletal and dental Class I relationship allowing for about 4 mm of vertical overlap of the maxillary anterior teeth over the mandibular anterior teeth (central and lateral incisors). The cuspid relationship is such that the cuspids fit vertically in the embrasure between the mandibular cuspids and the first premolars, assuming the appropriate normal anatomic height of the cuspid teeth. When the proper relationship is determined, the upper and lower dental arch casts are luted together with wax to maintain the above relationship. The relationship represents the desired post-surgical position of the upper and lower teeth. The presence and severity of wear on the teeth and anatomic abnormalities of the patient's teeth are noted. However, all surgical procedures are planned to allow for jaw repositioning with teeth of normal anatomic form, because basing the surgery on worn teeth or teeth of abnormal anatomic form will alter the vertical relationship of the jaws, particularly after the teeth have been repaired. Therefore, the method of the present invention includes allowances and timing for the restoration of the worn teeth or removal of anatomical abnormalities of the teeth, e.g., straightening, lengthening, shortening, or repositioning the teeth.

Figure 8:
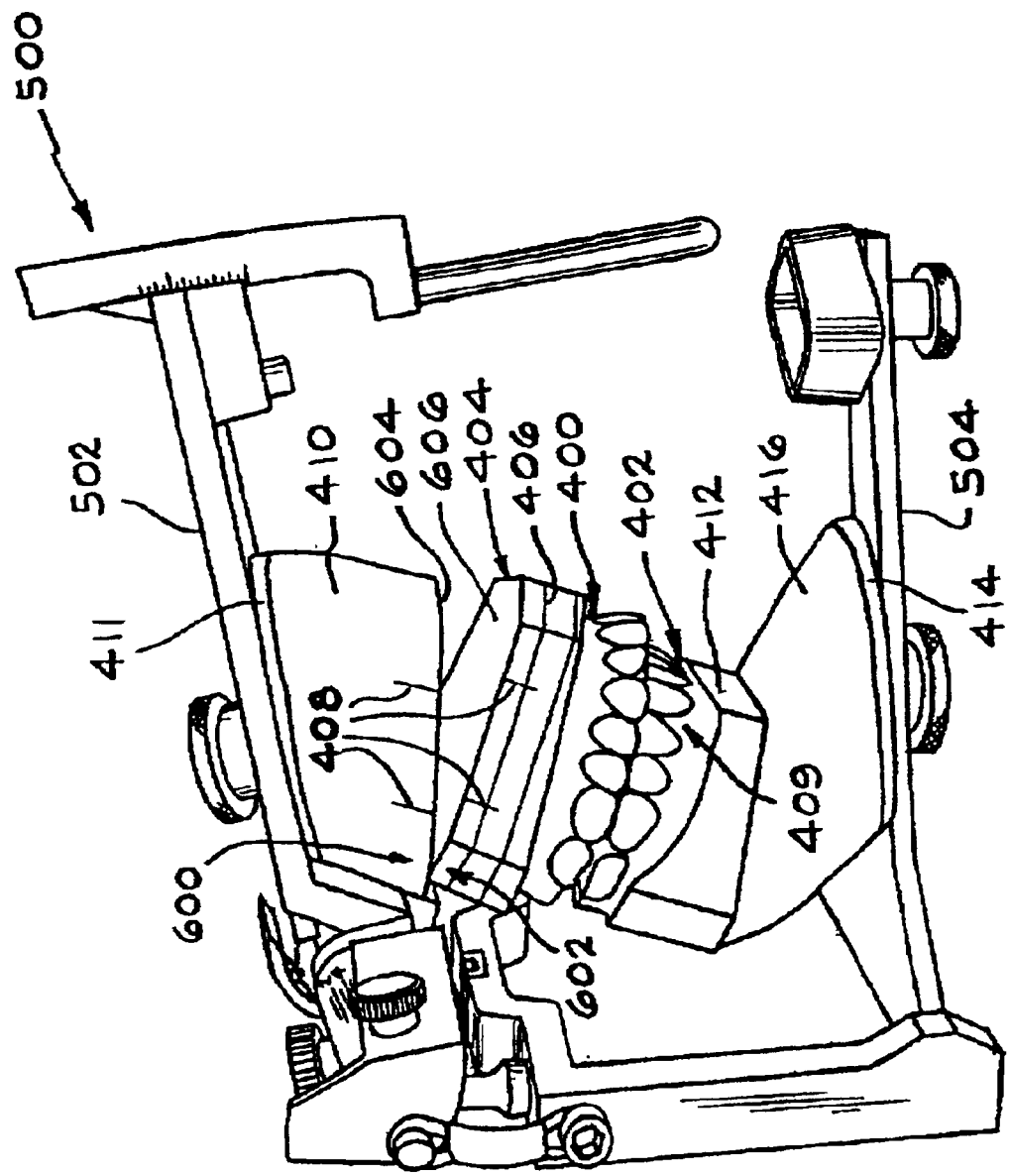
FIG. 8 is a perspective view of the upper dental arch 400 and lower dental arch 402 of a particular patient in a jaw joint artificial jaw simulator 500 set at the patient's true hinge axis and stable condylar position wherein the teeth 409 have been arranged in a skeletal and dental Class I relationship which reapproximates a functional bite. The Figure shows that to reapproximate the functional bite in the patient, a portion of the posterior maxillary bone has to be removed.

Next, with the dental casts still luted together in the desired post-surgical position, the upper member of the artificial jaw simulator is closed against the base of the upper dental arch cast so that the upper mounting stone is in contact with the base of the upper dental arch cast. This is shown in FIG. 8 which shows the upper dental arch 400 luted to the lower dental arch 402 mounted on lower mounting stone 412, which is mounted using settable material 416 to lower mounting plate 414 on lower member 504 of artificial jaw simulator 500, in the desired post-surgical position and the artificial jaw simulator 500 closed such that the upper mounting stone 410 with upper mounting plate 411, which is mounted on upper member 502 of artificial jaw simulator 500, is in contact with the base 404 attached to upper dental cast 400. The Figure also shows the horizontal reference lines 406 on the base 404 and the vertical reference lines 408 on both the base 404 and the upper mounting stone 410. In general, the posterior end 600 of the upper mounting stone 410 will contact the posterior end 602 of the base 404 attached to the upper dental arch 400 at an angle with the bottom surface 604 of the upper mounting stone 410 extending upward and away from the upper surface 606 of the base 404. The slope of the angle that is formed is noted. The slope of the angle reflects the amount of maxillary bone that will have to be removed to place the patient's maxillary and mandibular teeth in the desired post-surgery position. The amount of maxillary bone to be removed is determined by dry planing away the upper surface 606 of the base 404 attached to the upper dental cast 400 using a model trimmer, file, sandpaper, or the like (not shown) at the same slope as the angle formed by the bottom surface 604 of the mounting stone 410 as it extends away from the upper surface 606 of the base 404, until enough material from the upper surface 606 of the base 404 is removed such that the entire bottom surface 604 of the upper mounting stone 410 contacts the entire upper surface 606 of the base 404 attached to the upper dental arch cast 400 evenly while still maintaining the teeth in the desired post-surgical position.

Figure 9:
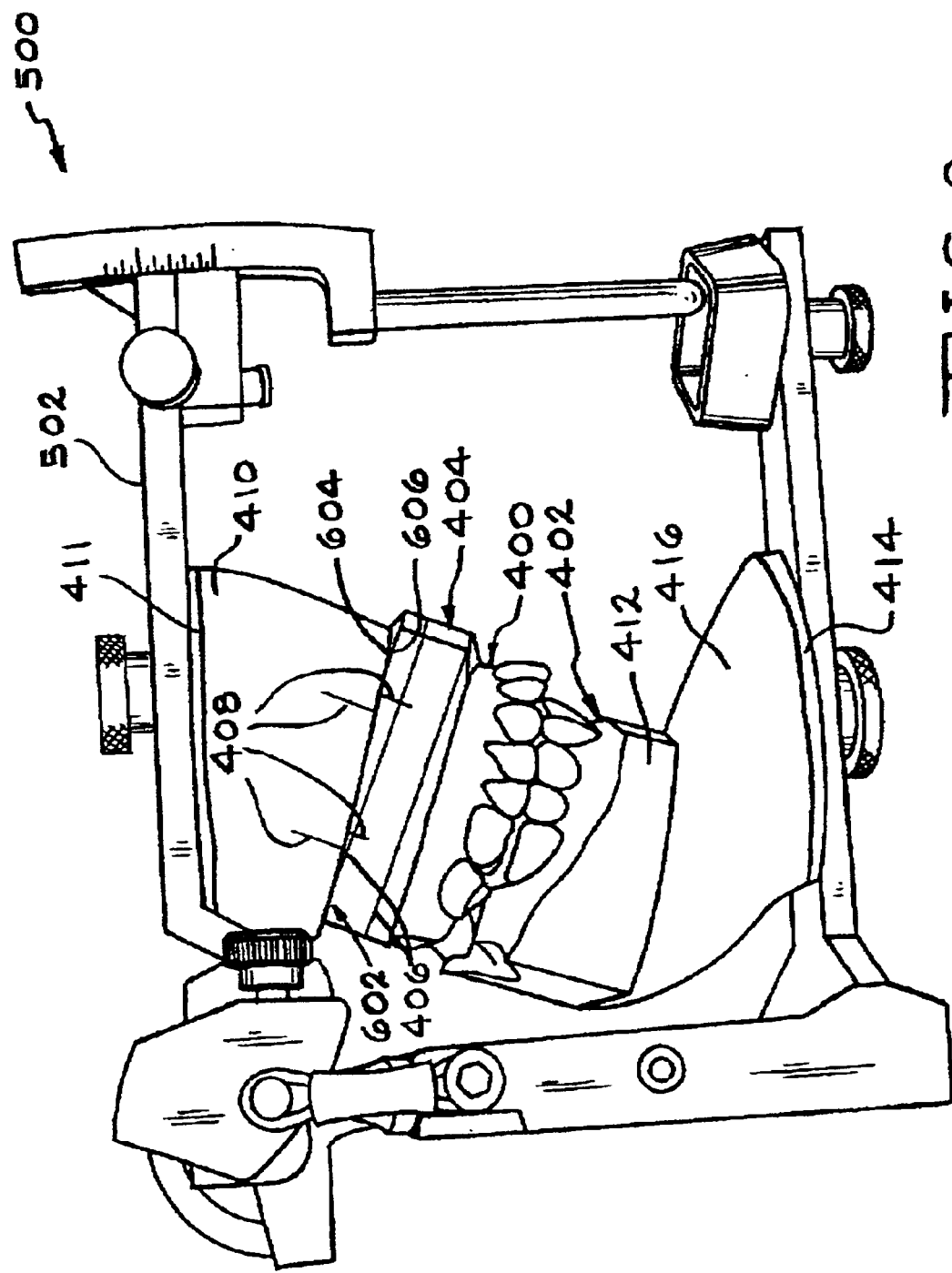
FIG. 9 is a perspective view of the upper dental arch 400 and lower dental arch 402 of the patient shown in FIG. 8 after sufficient maxillary bone has been removed to reapproximate the functional bite in the patient.

FIG. 9 shows the upper surface 606 of the base 404 with upper dental arch cast 400 in even contact with the bottom surface 604 of the upper mounting stone 410 with upper mounting plate 411 mounted to the upper member 502 of the artificial jaw simulator 500. The Figure also shows that in the desired post-surgical position, there is an offset between the vertical reference lines 408 on the base 404 and upper mounting stone 410. The amount of offset indicates the distance to which the maxilla has been advanced in order to achieve the desired post-surgical position.

Next, as illustrated by FIG. 9, the upper surface 606 of the base 404 attached to the upper dental cast 400 is then luted to the lower surface 604 of the upper mounting stone 410 with a thin film of wax (not shown). Measurement is then made from the horizontal reference line 406 on the base 404 near or at its posterior end 602 vertically to the where the luted upper mounting stone 410 contacts the base 404 and this measurement is subtracted from the original vertical height of 5 or 10 mm the base 404. The difference is the amount of posterior maxillary bone that is to be removed in order to restore a functional occlusion to the cranial base to mandible discrepancy in the patient, i.e., the amount of posterior maxillary bone that is to be removed in order to restore to the patient a functional bite while maintaining the stable condylar position criteria.

The above description illustrates the general planning procedure for determining the amount of posterior maxillary bone to remove to restore a functional bite to the patient. However, the above planning procedure can reveal other discrepancies in the mouth of the patient which must also be treated, managed, or corrected if a functional bite is to be restored to the patient. For example, if during the above planning procedure, horizontal discrepancies in the patient's jaw alignment are found which do not allow for the positioning of the upper dental arch cast of the maxilla over the lower dental arch cast of the mandible in a stable lateral relationship with the maxillary teeth over the mandibular teeth, then the upper dental arch cast of the maxilla is widened through the midline. This is done by sawing the upper dental arch cast of the maxilla through the midline between the central incisor teeth and widening the upper dental arch cast of the maxilla to the desired width by placing dental boarder wax between the two segments of the maxillary upper dental arch casts. The upper dental arch cast of the maxilla is then related to the lower dental arch casts of the mandible in the same manner as described above and the amount of midline maxillary bone that is to be added or removed to place the maxilla in a stable lateral relationship with the maxillary teeth over the mandibular teeth is noted.

As noted above, a review of the vertical reference lines on the model is performed to determine the degree of offset. If the offset shows that the upper dental arch cast of the maxilla has been retruded then the lower dental arch cast of the mandible is advanced the corresponding distance while leaving the upper dental arch cast of the maxilla in its original relationship. However, if the relationship demonstrates that the upper dental arch cast of the maxilla has been advanced then this advancement, in millimeters, must be assessed for its affects on facial soft tissue harmony when the advancement is performed on the patient. The required maxillary advancement may result in a deharmonizing effect on the facial contour of the patient in which case a surgical procedure is planned which will retrude the mandible as well as remove posterior maxillary bone. The same holds true for the previously described mandibular advancement procedure. As a general rule, it is preferable that surgical procedures not be planned which will result in retraction of the maxilla.

The importance of the model for planning the surgical procedure is that all measurements and determinations for restoring a functional bite in the patient while maintaining the stable condylar position are performed on the model. No adjustments are required to be made during the surgery itself. By planning the surgical procedure on the model reduces the likelihood of errors during the surgery and provides the surgeon with an exact procedure for performing the surgery.

Once the final jaw position for the patient has been established on the above model comprising the artificial jaw simulator with the patient's dental arch casts mounted thereon in the patient's true hinge axis of rotation and stable condylar position, then a surgical stint is fabricated for use in the operating room using the above model with the dental arch casts in the desired post-surgical position. The surgical stint acts as a guide to help the surgeon relate the patient's maxilla to the mandible in the desired post-surgery position during the surgery. The surgical stint is made with a cold-cure acrylic. A mixture of monomer and polymer is formed to a doughy consistency and a separating media is placed on surface of the upper and lower dental arch casts. The doughy acrylic is rolled into the shape of a solid cylinder long enough to follow the patient's entire maxillary dentition on the upper dental arch cast, i.e., from the patient's most posterior right tooth to the patient's most posterior left tooth. The artificial jaw simulator in which the dental arch casts are on is then closed and the acrylic allowed to harden.

Figure 10:
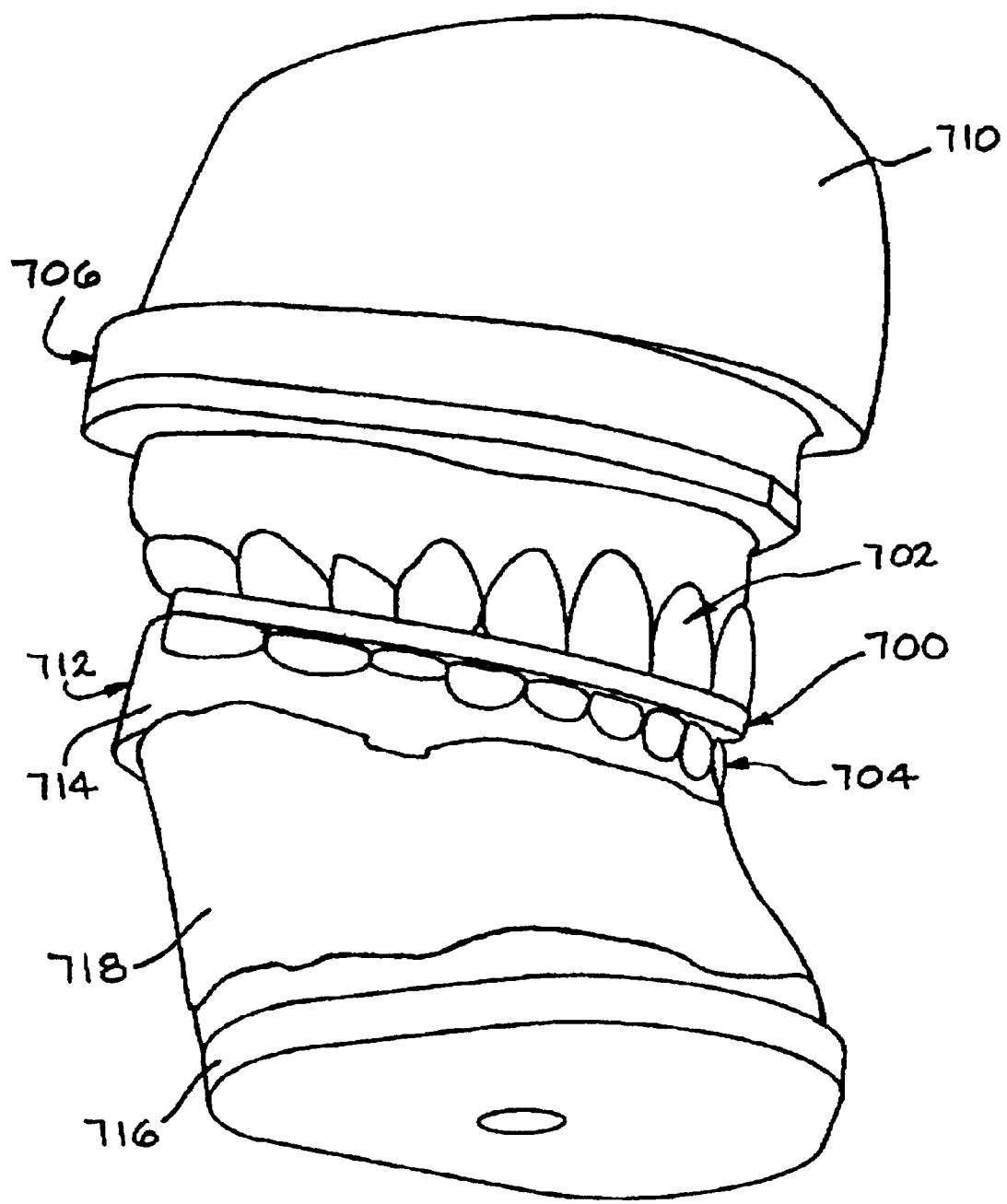
FIG. 10 is a perspective view of the upper dental arch 708 and lower dental arch 712 of a patient showing a surgical stint 700 between the teeth 702 of the upper dental arch 708 and the teeth 702 of the lower dental arch 704.

After hardening, the hardened acrylic is then removed from the dental arch casts as a hard solid horseshoe shaped wafer that fits over the upper and lower teeth of the patient and which approximates the patient's jaw into the desired post-surgical position. The wafer is trimmed with an acrylic bur so that about a 1 to 2 mm flange of acrylic is left on the external periphery of the wafer. FIG. 10 shows a surgical splint 700 in position between the teeth 702 of the upper dental arch cast 708 mounted on base 706 which is mounted on upper mounting stone 710 and the teeth 704 of the lower dental arch cast 712 mounted on lower mounting stone 714 and then mounted to lower mounting plate 716 using settable material 718.

If two jaw surgery is required, then two surgical splints are made: a final position surgical splint as described above for relating the maxilla to mandible following the final surgical procedure and an interim splint which is used to relate the mandible to the stable condyle-axis position for an interim surgery. The interim surgery is generally a surgical procedure for advancing or retruding the mandible in relation to the maxilla while maintaining the stable condylar position and the final surgical procedure is removing sufficient maxillary bone to restore a functional bite to the patient while maintaining the stable condylar position. The intermediate splint is made by relating an unaltered upper dental arch cast (no material representing maxillary bone has been removed from the base mounted to the upper dental arch cast) to the lower dental arch cast, which has either been advanced or retruded in order to achieve the stable jaw joint relationship. The upper and lower dental arch casts are then related to one another by means of the artificial jaw simulator in the manner as described above and an interim acrylic wafer or splint is fabricated as described above.

The fundamentals of the surgical procedure for Le Forte I osteotomy and Intraoral Sagittal Split osteotomy are standard in the art and are described in many texts on jaw surgery. In general, the maxilla is disarticulated from the skull using standard surgical methods and the amount of posterior maxillary bone determined on the model is removed from the posterior end of the maxilla. Additional surgery on the maxilla, e.g., widening the maxilla, or surgery on the mandible, e.g., lengthening or shortening the mandible, can be performed in the same surgery or in a prior surgery. After the appropriate amount of maxillary bone has been removed from the posterior end of the maxilla, the maxillary teeth are related to the mandibular teeth using the final position surgical stint, the maxillary bone attached to the skull with surgical plates, and with the final position surgical stint in place, the mouth is fixated shut for a time sufficient to enable healing of the maxilla to the skull.

After removal of the surgical stints, the patient is fitted with a post-surgery verification orthotic (which is the same or similar to the initial orthotic worn by the patient) to stable condylar position criteria, which the patient wears for time sufficient to verify that the surgery has properly related the maxilla and mandible to the stable condylar position.

In particular cases, after surgery it will be necessary to modify the patient's anterior maxillary teeth to achieve the proper overlap (anterior guidance) with the anterior mandibular teeth (central and lateral incisors) for effecting proper guidance of the mandible during mouth opening and closing. In some cases, the anterior maxillary teeth are elongated using tooth restoration methods well known in the art. In further cases, teeth with excessive or abnormal wear patterns are reconstructed. One skilled in the art would be able to readily determine what modifications to the teeth will be necessary to maintain the functional bite and stable condylar position post-surgery.

The novel element of the method of the present invention is that all surgical moves in the surgical procedure are predicated on the measurements obtained on the above model for the surgery wherein the model comprises an artificial jaw simulator with the patient's dental arch casts mounted thereon in the patient's true hinge axis of rotation and stable condylar position. By performing the surgical procedures based on the measurements determined on the model, no adjustment need be made at the time of the operation that has not been prescribed by the model for the surgery. The position of the jaw joints is not determined by manipulation of either the maxilla or mandible at the time of surgery except for that which has been determined on the model.

To summarize the general elements of the method for treating maxilla/cranial base to mandibular axis discrepancies in the temporomandibular joints such as caused by MTDS or facial/dental deformities: (1) all patient assessments and measurements are made from a jaw joint position which is the result of deprogramming the jaw joints into a stable condylar position using the craniomandibular orthopedic repositioning orthotic and which has meet the criteria of stable condylar position, (2) planning a surgical procedure comprising total maxillary osteotomy for realigning the patient's jaw joint into a functional bite while maintaining the stable condylar position on a model of the patient's mouth comprising an artificial jaw simulator and the patient's dental arch casts in the patient's true hinge axis of rotation in a stable condylar position and optionally wherein the tooth structure has been restored to normal biologic form, (3) preparing a surgical stint from the model in the desired post-surgical position for relating the patient's maxilla to the patient's mandible in the desired post-surgical position following the total maxillary osteotomy, (4) performing the surgical procedure on the patient as planned on the model and using the surgical stint prepared from the model to relate the patient's maxilla to the patient's mandible following the total maxillary osteotomy, and (5) following the surgery with a post-surgery verification orthotic (which is the same or similar to the initial orthotic worn by the patient), which is worn for a sufficient time by the patient post-surgery to stable condylar position criteria to verify that the surgery has properly related the maxilla and mandible to the stable condylar position. When necessary, the method further includes dental restoration of the anterior mandibular teeth (central and lateral incisors) to provide proper anterior guidance.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

I claim:

1. A method for treating maxilla/cranial base to mandibular axis discrepancies in the temporomandibular joints of a patient comprising (a) fitting an orthotic to the maxillary teeth of the patient so as to allow full coverage of all the maxillary teeth, wherein the orthotic has an anterior ramp to provide anterior guidance of the patient's mandible in excursive movements by contact of the superior surface of the anterior mandibular teeth of the patient with a posterior surface of the anterior ramp of the orthotic so as to allow for complete disclusion of the posterior mandibular teeth of the patient from the orthotic during eccentric jaw movements which over time deprograms the temporomandibular joints of the patient into a stable condylar position by stabilizing the condyles in their corresponding glenoid fossa sockets in the maxilla/cranial base;

(b) determining alignment of the mandible to the maxilla/cranial base in the temporomandibular joints of the patient after each condyle has been stabilized in its corresponding glenoid fossa socket by the orthotic;

(c) constructing a model of an upper dental arch of the patient with a base, which is parallel on all sides to the upper dental arch model and is delineated with horizontal and vertical reference lines, and a model of a lower dental arch of the patient with a base;

(d) mounting the base of the upper dental arch to an upper plate with mounting stone of an artificial jaw simulator and mounting the base of the lower dental arch to a lower plate with mounting stone of the artificial jaw simulator such that the true axis of rotation of the temporomandibular joints of the patient with the temporomandibular joints in the stable condylar position has been maintained and wherein the sides of each base are parallel and confluent to the artificial jaw simulator mounting plates;

(e) determining on the artificial jaw simulator mounted with the upper and lower dental arch models an amount of maxillary bone to be removed from the patient's maxilla in a surgical procedure wherein the maxilla is cut along a transverse plane superior to the maxillary teeth to separate the maxilla into an upper and a lower part which is sufficient to allow a jaw position in the patient when the upper and lower parts are joined after the amount of maxillary bone has been removed wherein the maxillary and mandibular teeth of the patient are re-approximated into a position coincidental to the stabilized jaw joint position with a functional bite wherein the anterior maxillary teeth provide anterior guidance of the mandible in excursive movements by contact of the lingual surface of the anterior maxillary teeth with the superior surface of the mandibular anterior teeth while allowing complete disclusion of the posterior maxillary and mandibular teeth during eccentric jaw movements and which at the same time maintains the temporomandibular joints in the stable condylar position;

(f) constructing a surgical stint of the functional bite in which the temporomandibular joints are in the stable condylar position to act as a guide for relating the maxilla to the mandible during the surgical procedure for removing the amount of maxillary bone from the patient determined in step (e);

(g) fitting the surgical stint into the mouth of the patient and performing the surgical procedure for removing the amount of maxillary bone from the patient's maxilla determined in step (e); and (h) immobilizing the patient's jaw following the surgical procedure with the surgical stint fitted to the patient's teeth so as to maintain the functional bite wherein the temporomandibular joints are in the stable condylar position and fixating the patient's mouth shut for a time sufficient for the upper and lower parts of the maxilla to heal, which treats the cranial base to the mandibular axis discrepancies in the temporomandibular joints.

2. The method of claim 1 wherein the surgical procedure further includes an interim surgical procedure selected from the group consisting of widening the patient's mandible, widening the patient's maxilla, retruding the patient's mandible, advancing the patient's mandible, retruding the patient's maxilla, advancing the patient's maxilla, and combinations thereof and an intermediate surgical stint is made to act as a guide for relating the maxilla to the mandible during the interim surgical procedure.

3. The method of claim 1 wherein the temporomandibular joints of the patient are stabilized by sequentially fitting orthotics to the patient's mouth wherein the anterior ramp of each orthotic in the sequence has been progressively elongated or wherein the orthotic is modified by elongating the anterior ramp or reducing the thickness of the orthotic covering the posterior maxillary teeth when needed to maintain complete disclusion of the posterior maxillary and mandibular teeth of the patient during eccentric jaw movements during the period of time for deprogramming the temporomandibular joints into the stable condylar position.

4. The method of claim 1 wherein the orthotic is modified by elongating the anterior ramp when needed to maintain complete disclusion of the posterior maxillary and mandibular teeth of the patient during eccentric jaw movements during the period of time for deprogramming the temporomandibular joints into the stable condylar position.

5. A surgical method for treating the cranial base to mandibular axis discrepancies in a patient comprising:

(a) constructing a model of an upper dental arch of the patient with a base, which is parallel on all sides to the upper dental arch model and is delineated with horizontal and vertical reference lines, and a model of a lower dental arch of the patient with a base;

(b) mounting the upper dental arch to an upper plate with mounting stone of an artificial jaw simulator and mounting the lower dental arch to a lower plate with mounting stone of the artificial jaw simulator such that the true axis of rotation of the temporomandibular joints of the patient with the temporomandibular joints in the stable condylar position has been maintained and wherein the sides of each base is parallel and confluent to the artificial jaw simulator mounting stones;

(c) determining on the artificial jaw simulator mounted with the upper and lower dental arch models an amount of maxillary bone to be removed from the patient's maxilla in a surgical procedure wherein the maxilla is cut along a transverse plane superior to the maxillary dentition to separate the maxilla into an upper and a lower part which is sufficient to allow a jaw position in the patient when the upper and lower parts are joined after the amount of maxillary bone has been removed wherein the dentition of the patient is re-approximated into a functional bite wherein the anterior maxillary teeth provide anterior guidance of the mandible in excursive movements by contact of the lingual surface of the anterior maxillary teeth with the superior surface of the mandibular anterior teeth while allowing complete disclusion of the posterior maxillary and mandibular teeth during eccentric jaw movements and which at the same time maintains the temporomandibular joints in the stable condylar position;

(d) constructing a surgical stint of the functional bite in which the temporomandibular joints are in the stable condylar position to act as a guide for relating the maxilla to the mandible during the surgical procedure for removing the amount of maxillary bone from the patient determined in step (c);

(e) fitting the surgical stint into the mouth of the patient and performing the surgical procedure for removing the amount of maxillary bone from the patient's maxilla determined in step (c); and (f) immobilizing the patient's jaw following the surgical procedure with the surgical stint fitted to the patient's teeth so as to maintain the functional bite wherein the temporomandibular joints are in the stable condylar position and fixating the patient's mouth shut for a time sufficient for the upper and lower parts of the maxilla to heal, which treats the cranial base to the mandibular axis discrepancies in the temporomandibular joints.

6. The method of claim 5 wherein the surgical procedure further includes an interim surgical procedure selected from the group consisting of widening the patient's mandible, widening the patient's maxilla, retruding the patient's mandible, advancing the patient's mandible, retruding the patient's maxilla, advancing the patient's maxilla, and combinations thereof and an intermediate surgical stint is made to act as a guide for relating the maxilla to the mandible during the interim surgical procedure.

7. A method for stabilizing the condylar positions in the temporomandibular joints of a patient with temporomandibular dysfunction syndrome comprising:

(a) providing an orthotic to the maxillary teeth of the patient so as to allow full coverage of all the maxillary teeth, wherein the orthotic is designed with an anterior ramp to provide anterior guidance of the patient's mandible in excursive movements by contact of the superior surface of the central and lateral incisors of the patient with a posterior surface of the anterior ramp of the orthotic so as to allow for complete disclusion of the posterior mandibular teeth from the orthotic of the patient during eccentric jaw movements which enables deprogramming the temporomandibular joints into stable condylar position;

(b) fitting the orthotic into the patient's mouth for a period of time sufficient to deprogram the temporomandibular joints into the stable condylar position;

(c) modifying the orthotic when needed to maintain complete disclusion of the posterior maxillary and mandibular teeth of the patient during eccentric jaw movements during the period of time for deprogramming the temporomandibular joints into the stable condylar position; and (d) measuring during the period of time for deprogramming the temporomandibular joints into the stable condylar position pain caused to the patient by the temporomandibular dysfunction, reproducibility of the patient's bite on the orthotic, neuromuscular tension of the patient's facial muscles, and the patient's condylar position indices, wherein the condylar positions in the temporomandibular joints of the patient are determined to be stabilized when the patient is free of the pain and has a reproducible bite on the orthotic, there is complete release of neuromuscular tension whereby the patient's facial muscles upon palpation show no signs of guarding, splinting, or tension, and the patient's condylar position indices are less than about 1 mm.

* * * * *